US010232083B2

(12) United States Patent
Chung et al.

(10) Patent No.: US 10,232,083 B2
(45) Date of Patent: Mar. 19, 2019

(54) MIMETIC TISSUE STRUCTURE CONTAINING EXTRACELLULAR MATRIX PROTEIN-BONE MINERAL COMPLEX AND METHOD FOR MANUFACTURING SAME

(71) Applicant: NANO INTELLIGENT BIOMEDICAL ENGINEERING CORPORATION CO. LTD., Seoul (KR)

(72) Inventors: Chong-Pyoung Chung, Seoul (KR); Yoon Jeong Park, Seoul (KR); Jue-Yeon Lee, Gyeonggi-do (KR)

(73) Assignee: NANO INTELLIGENT BIOMEDICAL ENGINEERING CORPORATION CO. LTD., Seoul (KR)

( * ) Notice: Subject to any disclaimer, the term of this patent is extended or adjusted under 35 U.S.C. 154(b) by 544 days.

(21) Appl. No.: 14/779,339

(22) PCT Filed: Apr. 1, 2014

(86) PCT No.: PCT/KR2014/002772
§ 371 (c)(1),
(2) Date: Sep. 23, 2015

(87) PCT Pub. No.: WO2014/163371
PCT Pub. Date: Oct. 9, 2014

(65) Prior Publication Data
US 2016/0058909 A1    Mar. 3, 2016

(30) Foreign Application Priority Data

Apr. 2, 2013 (KR) ........................ 10-2013-0035850

(51) Int. Cl.
*A61L 27/36* (2006.01)
*A61L 27/02* (2006.01)
(Continued)

(52) U.S. Cl.
CPC ........... *A61L 27/3608* (2013.01); *A61L 27/02* (2013.01); *A61L 27/22* (2013.01); *A61L 27/24* (2013.01);
(Continued)

(58) Field of Classification Search
None
See application file for complete search history.

(56) References Cited

U.S. PATENT DOCUMENTS 6,428,579 B1 * 8/2002 Valentini ............. A61F 2/30767
427/2.13
7,556,649 B2 * 7/2009 Moehlenbruck .... A61L 27/3612
424/93.7
(Continued)

FOREIGN PATENT DOCUMENTS

KR    100739528 B1    7/2007
KR    101000537 B1    12/2010
(Continued)

OTHER PUBLICATIONS

English Translation of WO2013009057.*
(Continued)

*Primary Examiner* — Julie Wu
*Assistant Examiner* — Douglas F White
(74) *Attorney, Agent, or Firm* — Hultquist, PLLC; Steven J. Hultquist (57) ABSTRACT

Provided are a tissue structure mimetic used for regenerating a tissue and a method for manufacturing the same, and more particularly, a 3-dimensional tissue structure mimetic which consists of a complex of extracellular matrix protein and bone mineral, wherein the complex is specifically bound to a regeneration-functional peptide to thereby be capable of implementing environment of a tissue requiring restoration, and a method for manufacturing the same. In the tissue (Continued)

structure mimetic according to the present invention, bone mineral components are finely dispersed in the extracellular matrix protein to have excellent mechanical strength of the tissue structure mimetic and conductivity which provides a migration path of cells involved in tissue regeneration. Further, environment of the tissue may be implemented by the peptide contained in the tissue structure mimetic to finally remarkably increase tissue regeneration capacity.

10 Claims, 3 Drawing Sheets

(51) Int. Cl.
    *A61L 27/22*     (2006.01)
    *A61L 27/24*     (2006.01)
    *B29B 11/08*     (2006.01)
    *B29B 13/04*     (2006.01)
    *B29L 31/00*     (2006.01)

(52) U.S. Cl.
    CPC .......... *A61L 27/3633* (2013.01); *B29B 11/08* (2013.01); *B29B 13/04* (2013.01); *B29K 2005/00* (2013.01); *B29K 2489/00* (2013.01); *B29L 2031/7532* (2013.01)

(56) References Cited

U.S. PATENT DOCUMENTS

| | | | |
|---|---|---|---|
| 8,834,928 B1* | 9/2014 | Truncale | C12N 5/0663 424/484 |
| 9,352,003 B1* | 5/2016 | Semler | A61K 35/32 |
| 2005/0177249 A1* | 8/2005 | Kladakis | A61L 27/48 623/23.74 |
| 2005/0233454 A1 | 10/2005 | Nies et al. | |
| 2008/0025950 A1* | 1/2008 | Prestwich | A61L 27/20 424/93.1 |
| 2013/0022548 A1* | 1/2013 | Bennett | A61K 49/12 424/9.3 |
| 2014/0023723 A1* | 1/2014 | Leach | A61L 27/3633 424/577 |

FOREIGN PATENT DOCUMENTS

| | | |
|---|---|---|
| KR | 1020110121401 A | 11/2011 |
| KR | 1020130006194 A | 1/2013 |
| KR | 101229436 B1 | 2/2013 |
| WO | 2005089826 A1 | 9/2005 |
| WO | 2007089084 A1 | 8/2007 |
| WO | 2009156760 A2 | 12/2009 |
| WO | WO-2013009057 * | 1/2013 |

OTHER PUBLICATIONS

English Translation of KR10 1000537.*
Anselme, K., "Osteoblast adhesion on biomaterials", "Biomaterials", Apr. 2000, pp. 667-681, vol. 21.
Casser-Bette, M., et al., "Bone formation by osteoblast-like cells in a three-dimensional cell culture", "Calcified Tissue International", Jan. 1990, pp. 46-56, vol. 46.
Grzesik, W., et al., "Bone matrix RGD glycoproteins: immunolocalization and interaction with human primary osteoblastic bone cells in vitro", "Journal of bone and Mineral Research", Apr. 1994, pp. 487-496, vol. 9, No. 4.
Pal, S., "Mechanical Properties of Biological Materials", "Design of Artificial Human Joints & Organs", Jan. 8, 2013, pp. 23-40, Publisher: Springer Science and Business Media New York.

* cited by examiner

Example 1　　　　Example 4　　　　Other company's

MIMETIC TISSUE STRUCTURE CONTAINING EXTRACELLULAR MATRIX PROTEIN-BONE MINERAL COMPLEX AND METHOD FOR MANUFACTURING SAME

CROSS-REFERENCE TO RELATED APPLICATIONS

This application is a U.S. national phase under the provisions of 35 U.S.C. § 371 of International Patent Application No. PCT/KR14/02772 filed Apr. 1, 2014, which in turn claims priority of Korean Patent Application No. 10-2013-0035850 filed Apr. 2, 2013. The disclosures of such international patent application and Korean priority patent application are hereby incorporated herein by reference in their respective entireties, for all purposes.

TECHNICAL FIELD

The present invention relates to a tissue structure mimetic used for regenerating a tissue and a method for manufacturing the same, and more particularly, to a 3-dimensional tissue structure mimetic which consists of a complex of extracellular matrix protein and bone mineral, or an extracellular matrix protein-bone mineral complex and a regeneration-functional peptide, and a method for manufacturing the same.

BACKGROUND ART

Hard tissues including bone and teeth in a human body include approximately 80% of inorganic material and water, and 20% of organic materials, and the organic materials consist of 80% of collagen protein, and 20% of non-collagen protein. These protein components contribute to maintaining generation, structural strength and elasticity of hard tissue, inducing attachment of hard tissue-forming cells such as osteoblast cell, and the like, and functioning as a matrix which orientates inorganic ion components configuring hard tissue components (Anselme, Osteoblast adhesion on biomaterials, Biomaterials, 21 (7): 667-81, 2000).

Various researches for developing human-derived proteins as medical biomaterials for substituting or replacing bio-functions have been conducted, and various bio-materials that mimic natural tissue have also been developed according to development of a biotechnological technique.

The bio-materials need to be biologically suitable, and are divided into three classes depending on the degree of contact with a human body. A first class includes materials that are not in contact directly with a human body or do not change fluid composition even though they are in contact with human, a second class includes materials that are in contact intermittently or in a short time such as within 24 hours, and a third class which is a transplant includes materials that are inserted into a human body to be in continuous contact with the tissue, in particular, the third class materials are required to guarantee complete stability with respect to a human body (regulations regarding approval, inspection, examination, etc., of a medical device by the Food and Drug Administration). These third class materials may be divided into bioinert materials that maintain a form and a shape without causing an immune response after transplantation according to biological reaction forms with surrounding tissues, bioactive materials that are directly bound to surrounding tissues to provide biological functions, and biodegradable materials that are slowly decomposed in body after transplantation and substituted with autologous generation tissue.

In addition, biostability and biocompatibility need to be considered in the biomaterials. A representative method using natural tissue as the biomaterial is allograft. However, in accordance with recent development of molecular biology, protein engineering, and the like, it is possible to treat the natural tissue itself to be directly used, or to extract target tissue components (Medical polymer material, Korea Institute of Science and Technology Information).

Figure 1:
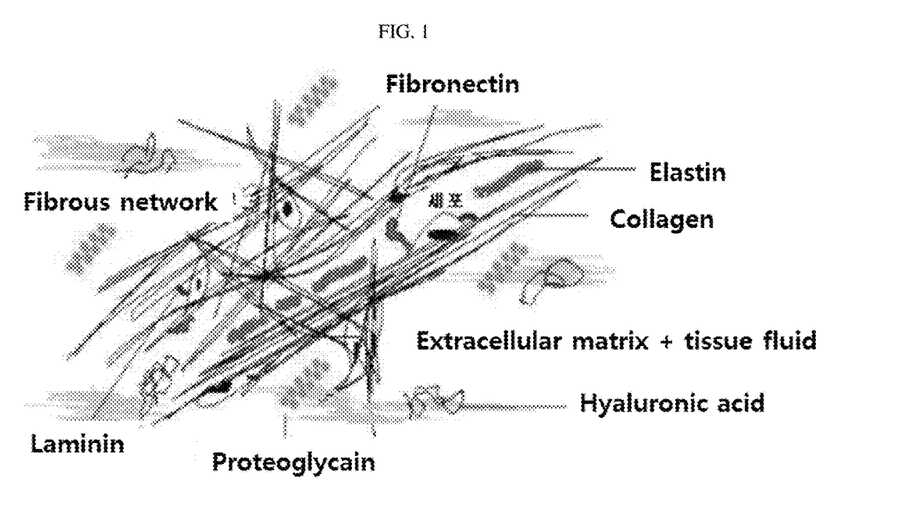
FIG. 1 is a diagram showing a tissue constitution formed by binding cells to a structure forming collagen which is a fibrous protein, and an extracellular matrix consisting of sugar, minerals, and the like, in body fluid which is an ionic solution.

A representative natural polymer used as the biomaterial is an extracellular protein, in particular, collagen, fibronectin, vitronectin, and the like, are representative examples. For example, peptide sequence consisting of arginine (R)-glycine (G)-aspartic acid (D) that induces cell adhesion included in collagen or fibronectin, and therefore, when RGD peptide is artificially arranged on a surface of the biomaterial, environment for inducing the surface of the material and the adhesion of the cell is provided to mimic function of the natural tissue by binding with surrounding cells (FIG. 1) (Grzesik et al., Bone Matrix RGD Glycoproteinsimmunolocalization and interaction with human primary osteoblastic bone cells in vitro, J Bone Miner Res, 9: 487-496, 1994).

Further, these collagen proteins are present in soft tissue such as skin dermis layers, mucosa layers, and the like, and these collagen proteins form bundles in subcutaneous tissue and bind to inorganic ions in body fluid components to maintain elasticity of the dermis and mucosal tissue and to function as a base matrix for the proliferation of cells and formation of soft tissue (Casser-Bette et al., *Bone formation by osteoblast-like cells in a three dimensional cell culture*, *Calcif Tissue Int*, 46: 46-56, 1990). Therefore, research into biomaterials made of apatite-containing inorganic materials or manufactured by coating inorganic materials on surfaces of polymers or proteins so as to be used as materials for restoration of bone tissue defect or subcutaneous tissue has been continuously conducted.

However, existing tissue regeneration technology in which apatite-containing inorganic materials or synthetic or natural polymers, in particular, collagen-derived proteins are applied alone has limited effects in view of a final biomechanical role of tissue, that is, complete restoration of biological functions.

An object of the biomaterial for tissue regeneration is to maintain biomechanical role of damaged tissue after transplantation, and accordingly, to restore morphological and physiological functions of tissue. Therefore, apatite transplant materials for being used as the biomaterial need to be directly usable, promote rapid tissue generation and revascularization in tissue, and maintain support and continuity of tissue, and not to cause an immune reaction, and the like, to thereby basically satisfy these conditions (Medical polymer material, Korea Institute of Science and Technology Information).

In the apatite-protein structure, even though the structure is swollen by body fluid, bone minerals included in the structure needs not to be separated to the outside of the structure in view of structural stability, unlike the existing simply mixed structure. When the apatite is not separated from the structure but stably contained in the structure, the apatite finally acts as a conductor which promotes stability when cells move. In addition, the protein structure containing apatite also needs to contribute to the above-described tissue generation capacity and revascularization in tissue. That is, the manufactured apatite-protein structure needs to provide conductivity in cell proliferation and tissue formation. However, these structures themselves function as a medium having bone conductivity; however, lack tissue inducing power for initial tissue formation that is essential to shorten a treatment period.

Researches into technology of using bioactive materials such as extracellular matrix proteins, tissue growth factors, or tissue formation proteins, together with tissue regeneration materials, in the structure so that the structure is mimicked to be close to tissue environment while overcoming the above-described disadvantages were conducted, and products such as INFUSE (containing BMP-2), GEM21S (containing PDGF), and the like, were developed (Anselme, Osteoblast Adhesion on Biomaterials, Biomaterials, 21 (7), 667-681, 2000). However, these proteins do not stably fix to the structure, and are instead discharged from the structure and degraded at the time of being exposed to blood of body, such that it is difficult to continuously maintain activity of tissue regeneration.

Accordingly, in order to overcome the above-described problems, a mimic having a structure and providing functions of conducting cell movement in the tissue at the time of filling biomaterials into damaged tissue while implementing a tissue environment, and finally inducing a regeneration function by protein or bioactive materials is required to be developed.

Therefore, the present inventors made an effort to solve the problems of the related art as described above, developed a tissue structure mimetic in which extracellular matrix protein and bone mineral component are organically bound to each other so as to have a composition that is similar to that of hard tissue constitution, found that the tissue structure mimetic is formable according to shapes of a transplant area as well as hard tissue to provide a high effect for tissue regeneration, and completed the present invention.

DISCLOSURE

Technical Problem

An object of the present invention is to provide a 3-dimensional tissue structure mimetic in which a micro-sized apatite-based bone mineral capable of enhancing mechanical strength is stably incorporated into an extracellular matrix protein to thereby be suitable for tissue regeneration, and a method for manufacturing the same.

In order to achieve the foregoing objects, the present invention provides a method for manufacturing a tissue structure mimetic, the method comprising the steps of: (a) forming a mixture of an extracellular matrix protein and bone mineral particles; (b) repeating freezing and g thereby aligning a structure of protein; (c) crosslinking by adding a monosaccharide solution; and (d) performing lyophilization.

In addition, the present invention also provides a method for manufacturing a tissue structure mimetic, the method comprising the steps of: (a) forming a mixture of an extracellular matrix protein and bone mineral particles; (b) repeating freezing and thawing thereby aligning a structure of protein; (c) crosslinking by adding a monosaccharide solution; (d) binding a regeneration-functional peptide to said complex of extracellular matrix protein and bone mineral; and (e) performing lyophilization.

Further, the present invention provides a tissue structure mimetic manufactured by the method for manufacturing a tissue structure mimetic including: (a) forming a mixture of an extracellular matrix protein and bone mineral particles; (b) repeating freezing and thawing thereby aligning a structure of protein; (c) crosslinking by adding a monosaccharide solution; and (d) performing lyophilization.

In addition, the present invention provides a tissue structure mimetic manufactured by the method for manufacturing a tissue structure mimetic including: (a) forming a mixture of an extracellular matrix protein and bone mineral particles; (b) repeating freezing and thawing thereby aligning a structure of protein; (c) crosslinking by adding a monosaccharide solution; (d) binding a regeneration-functional peptide to said complex of extracellular matrix protein and bone mineral; and (e) performing lyophilization.

BEST MODE

As it is not defined in other ways, all technical and scientific terms used in the present specification have the same meaning as being generally appreciated by those skilled in the art to which the present invention pertains. In general, the nomenclature used in the present specification is well known in technical fields and generally used.

According to an aspect of the present invention, the present invention provides a method for manufacturing a tissue structure mimetic, the method comprising the steps of: (a) injecting a mixture of an extracellular matrix protein and micro-sized bone mineral particles into a predetermined size of a forming mold; (b) repeating quick-freezing and thawing thereby aligning a structure of protein; (c) crosslinking by adding a monosaccharide solution; and (d) performing lyophilization.

In the present invention, the extracellular matrix protein e tissue structure mimetic may be selected from collagen, hyaluronic acid, elastin, chondroitin sulfate, or fibroin. The extracellular matrix protein may include all proteins such as a protein derived from human or animal, and a recombinant protein produced in a microorganism.

The bone mineral component usable in the present invention may include bio-derived bone mineral powders that are derived from allograft, bovine bone, equine bone, swine bone, and the like, and synthetic hydroxide apatite, tricalcium phosphate micro powders, and the like as all kinds of apatite-based materials used in the art.

The bone mineral component and the extracellular matrix protein may be surface-modified so that a regeneration-functional peptide is easily attached thereto.

In the present invention, a ratio between the bone mineral component and the extracellular matrix protein may be variously changed. For generation of a hard tissue such as a bone tissue, a content of the bone mineral component is preferably 80% or more based on the entire content, more preferably, 80 to 95%. For generation of a soft tissue such as a subcutaneous tissue, a content of the bone mineral component is preferably 35% or less based on the entire content, more preferably, 5 to 35%. When a content of the bone mineral component is increased, mechanical strength is also increased, such that a tissue structure mimetic having a ratio which is suitable for a structural characteristic of each tissue needs to be used.

The tissue structure mimetic according to the present invention is manufactured by aligning a protein structure of the mixture of an extracellular matrix protein and micro-sized bone mineral particles through temperature change to achieve physical cross-linkage, adding sugar solutions such as monosaccharides, preferably, ribose, and the like, to achieve chemical cross-linkage, and performing lyophilization, such that the tissue structure mimetic has a structure in which bond minerals are collected in a protein network.

In the present invention, step of (b) aligning a structure of protein means that as positions of the protein chains become close to each other, a hydrophobic bond, a hydrogen bond, and the like, between protein chains, are formed to align arrangement of protein chains, which make the structure of protein be stabilized.

As compared to a structure manufactured by simple mixing and lyophilization, the tissue structure mimetic manufactured by the method as described above has increased elasticity, and bone mineral component is not discharged even though it contacts body fluid, and the like, such that a structure of the tissue structure mimetic may be stably maintained.

The peptide that is specifically bound to the extracellular matrix protein according to the present invention may include elastin-attached peptide, hyaluronic acid-attached peptide, and the like. These peptides allow synthesis to have free amino groups or cysteine groups at N-terminal, or have affinity to protein forming a structure even by physical mixing, thereby providing stability.

As the elastin-attached peptide, any one of QSIDTNSHQDH, TEDVEKDQSE, EEHRQSFEDEQ, NEQQTLSRV, SRMNKNGDK, NKKPKNPKRRT, KKAQEAKNAE, EARKAEEARI, DDATSQLNGN, LKAASKDDAD, LSTLSALQQK, ADARFADAAA, KSNQQSNSQN, and GSKGGKGKSS may be used, but the present invention is not limited thereto.

As the hyaluronic acid-attached peptide, any one sequence of CRLLGLSLA, CSYGWVGDGFV, VRYPIRAPR, VISRISPNPRC, KQKIKHVVKLK, KLRCQLAKKKQ, CRYRYEPAL, VSPRRVRVKWWK, VRSYGPRHRRLHR, CNGRCGGRRAVL, GSPRVKWTFLS, SRGRGGRGVRVKVNEAYRFR, ILREAERRRQ, EKPGDRFDRDRPLR, PLRGRGGPRGGMRGRGRGG, PRPGRGARGGTRGGRG, GRIRRAENYG, KNLSKVVAR, RPRGCGRGRGGNQGRGRGGGINK, KAVVIHKSK, RQQQLQRKRRDE, and RPLRGRGGPRGGMRGRGRGGPGNR may be used, but the present invention is not limited thereto.

Meanwhile, mechanical strength of the tissue structure mimetic may be controlled according to time, temperature, and repetitive number of freezing and thawing, and further, final strength of the tissue structure mimetic may be changed according to concentration and reaction time of a monosaccharide solution.

In step (b) of the present invention, arrangement of the extracellular matrix protein may be aligned by repeating freezing and thawing three to five times, wherein the freezing and thawing process means leaving the mixture of an extracellular matrix protein and micro-sized bone mineral particles at −80° C. for 2 hours, and at room temperature (15° C. to 30° C.) for 1 hour. When the freezing and thawing process is performed less than three times, the alignment of the structure is not sufficiently performed, and when the freezing and thawing process is performed inure than five times, the alignment of the structure of the extracellular matrix protein stops.

A reaction concentration of the monosaccharide solution in step (c) of the present invention may be 2.5% (w/w) to 5% (w/w), and when the concentration is less than 2.5% (w/w), a cross-linkage reaction is not sufficiently performed, and when the concentration is more than 7.5% (w/w), a cross-linkage reaction is not increased in proportion to the concentration.

As the monosaccharide used in the present n, aldose, ketose, derivatives of aldose, derivatives of ketose, glycerone, threose, erythrose, lyxose, xylose, arabinose, ribose, allose, altrose, glucose, fructose, mannose, gulose, idose, and the like, may be used. Other monosaccharides as well as monosaccharides exemplified in Examples may be easily applied by a person skilled in the art.

In the present invention, the peptide that is capable of being specifically bound to the extracellular matrix protein is cross-linked by monosaccharide, and is absorbed and fixed to the tissue structure mimetic, to thereby obtain a structure including the peptide fixed thereto.

In the case of chemically fixing the peptide, a fixed amount of the peptide is preferably 1 to 1000 mg based on unit weight (g) of the tissue structure mimetic. More preferably, the peptide consists of 5 to 30 amino acids, and a fixed amount of the peptide is preferably 100 to 500 mg based on unit weight (g) of the tissue structure mimetic.

EXAMPLE

Hereinafter, the present invention will be described in detail with reference to the following Examples. However, the following examples are only for exemplifying the present invention, and it will be obvious to those skilled in the art that the scope of the present invention is not construed to be limited to these examples. Therefore, the substantial scope of the present invention will be defined by the accompanying claims and their equivalents.

Example 1: Structure that Consists of Bovine-Derived Bone Mineral Particles and Collagen (Containing 10% Collagen)

Bovine-derived bone mineral particles were manufactured to have a particle size of 0.2 to 0.4 mm. 2% (w/v) swine skin-derived collagen solution (500 ul) dissolved in 0.1M acetic acid was mixed with a bone mineral component (90 mg) so that a content of the collagen was 10% of the total weight ratio. The mixture was filled in a forming mold. Then, a freezing and thawing process including freezing at −80° C. for 2 hours and thawing at room temperature (15 to 30° C.) for 1 hour, was repeated three times. Then, the mixture was left in a water bath including saturated ammonia vapor to neutralize acetic acid included in the collagen-bone mineral mixture. The neutralized collagen-bone mineral complex was reacted with 5% ribose solution for 24 hours, and residual ribose was washed with purified water. After being washed, lyophilization was performed to obtain a tissue structure mimetic containing the collagen and the bone mineral component.

Example 2: Structure that Consists of Equine-Derived Bone Mineral Particles and Collagen (Containing 10% Collagen)

Equine-derived bone mineral particles were manufactured to have a particle size of 0.2 to 0.4 mm. 2% (w/v) swine skin-derived collagen solution (500 ul) dissolved in 0.1M acetic acid was mixed with a bone mineral component (90 mg) so that a content of the collagen was 10% of the total weight ratio. The mixture was filled in a forming mold. Then, a freezing and thawing process including freezing at −80° C. for 2 hours and thawing at room temperature (15 to 30° C.) for 1 hour, was repeated three times. Then, the mixture was left in a water bath including saturated ammonia vapor to neutralize acetic acid included in the collagen-bone mineral mixture. The neutralized collagen-bone mineral complex was reacted with 5% ribose solution for 24 hours, and residual ribose was washed with purified water. After being washed, lyophilization was performed to obtain a tissue structure mimetic containing the collagen and the bone mineral component.

Example 3: Structure that Consists of Bovine-Derived Bone Mineral Particles and Collagen (Containing 80% Collagen)

Bovine-derived bone mineral particles were manufactured to have a particle size of 0.05 to 0.1 mm. 2% (w/v) swine skin-derived collagen solution (4 ml) dissolved in 0.1M acetic acid was mixed with a bone mineral component (200 mg) so that a content of the collagen was 80% of the total weight ratio. The mixture was filled in a forming mold. Then, a freezing and thawing process including freezing at −80° C. for 2 hours and thawing at room temperature (15 to 30° C.) for 1 hour, was repeated three times. Then, the mixture was left in a water bath including saturated ammonia vapor to neutralize acetic acid included in the collagen-bone mineral mixture. The neutralized collagen-bone mineral complex was reacted with 5% ribose solution for 24 hours, and residual ribose was washed with purified water. After being washed, lyophilization was performed to obtain a tissue structure mimetic containing the collagen and the bone mineral component.

Example 4: Structure that Consists of Bovine-Derived Bone Mineral Particles and Collagen (Containing 70% Collagen)

Bovine-derived bone mineral particles were manufactured to have a particle size of 0.2 to 0.4 mm. 2% (w/v) swine skin-derived collagen solution (3.5 ml) dissolved in 0.1M acetic acid was mixed with a bone mineral component (30 mg) so that a content of the collagen was 70% of the total weight ratio. The mixture was filled in a forming mold. Then, a freezing and thawing process including freezing at −80° C. for 2 hours and thawing at room temperature (15 to 30° C.) for 1 hour, was repeated three times. Then, the mixture was left in a water bath including saturated ammonia vapor to neutralize acetic acid included in the collagen-bone mineral mixture. The neutralized collagen-bone mineral complex was reacted with 5% ribose solution for 24 hours, and residual ribose was washed with purified water. 20 mg of elastin attached-peptide (EEHRQSFEDEQ) was dissolved in 50 ul of phosphate buffer. Then, the resultant solution was added to the tissue structure mimetic filled in each forming mold, and left at refrigeration temperature (4 to 8° C.) for 24 hours. Lyophilization was performed to obtain the tissue structure mimetic containing the collagen, the bone mineral component, and the peptide.

Experimental Example 1: Observation of Structure of Tissue Structure Mimetic The tissue structure mimetic manufactured by Examples 1 to 4 and the other company's product (BioOss-collagen, Geistlich, Switzerland) as a control group were observed by a field emission scanning electron microscope (FE-SEM). Each tissue structure mimetic was coated with gold, and observed by the field emission scanning electron microscope (FE-SEM), Jeol, S-4700, Japan.

Figure 2:
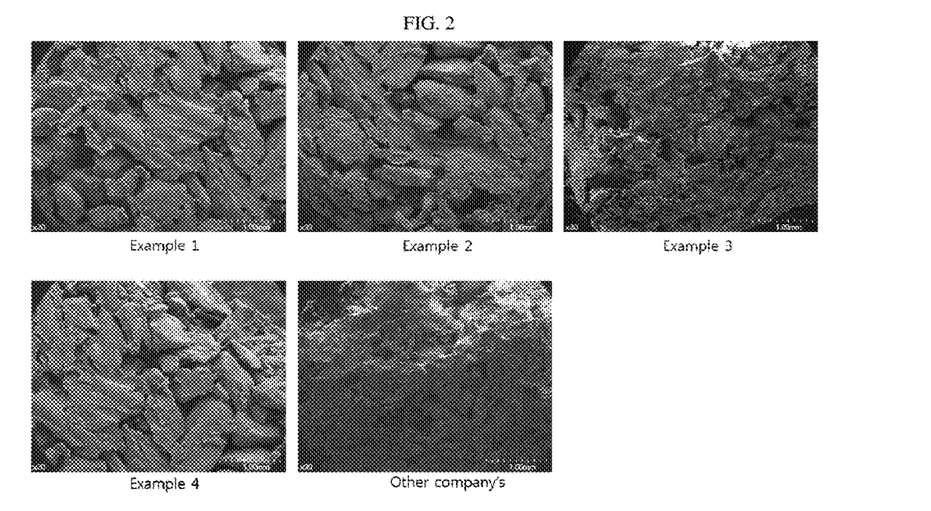
FIG. 2 is images of tissue structures mimic observed by a field emission scanning electron microscope.

FIG. 2 is images of each of the tissue structure mimetic observed by the field emission scanning electron microscope. It could be observed that the bone mineral component was mixed in a network of the extracellular matrix protein in the tissue structure mimetic manufactured by Examples 1 to 4. Meanwhile, the bone mineral component was not easily observed in the other company's product.

Experimental Example 2: Measurement of Change in Compressive Strength of Tissue Structure Mimetic According to the Repetitive Number of Freezing and Thawing In order to observe an effect of mechanical strength on the tissue structure mimetic of Example 1 according to the repetitive number of freezing and thawing, compressive strength of the tissue structure mimetic manufactured by changing the repetitive number of freezing and thawing were measured. In the test method, span was controlled so as to meet a sample size according to ASTM D 638. Measurement device was UTM (WL2100), and measurement speed was 5 mm/min. 200N load cell was used, and the span (gauge length) was set to be 10 mm to measure compressive strength.

Figure 3:
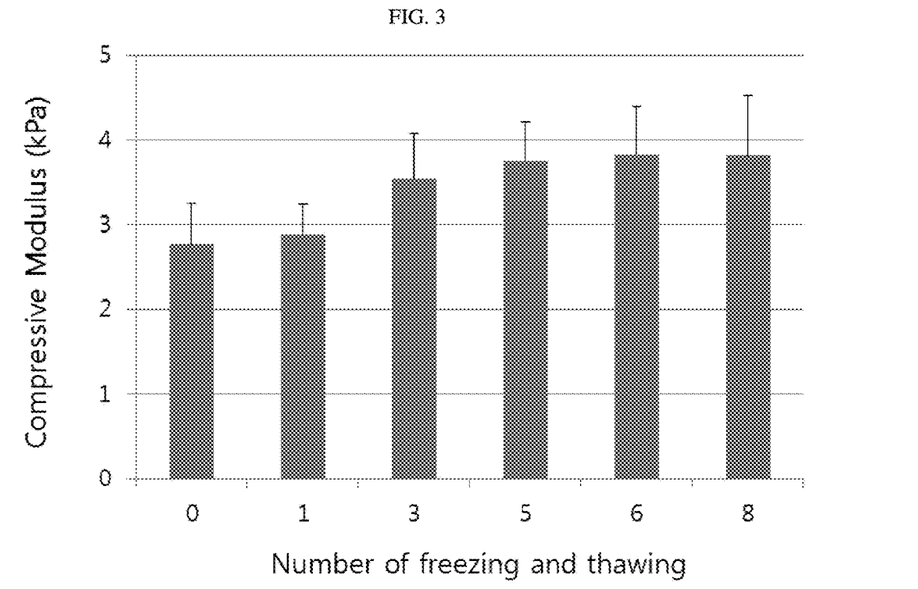
FIG. 3 is a graph showing change in compressive strength of the tissue structure mimetic depending on the repetitive number of freezing and thawing.

Table 1 shows results of compressive strength of the tissue structure mimetic manufactured by changing the repetitive number of freezing and thawing. When the repetitive number of freezing and thawing was 0, the compressive strength was 2.77 kPa; however, when the compressive strength was 3.54 kPa when the repetitive number of freezing and thawing was 3, and 3.75 kPa when the repetitive number of freezing and thawing was 5, which was increased as the number of freezing and thawing was increased. When the freezing and thawing was repeated six or more times, the compressive strength was 3.82 kPa, which did not largely increase. It could be appreciated from FIG. 3 made by summarizing the results of Table 1 as a graph that the compressive strength was largely increased when the freezing and thawing was repeated three to five times.

TABLE 1 compressive strength according to the repetitive number of freezing and thawing

| repetitive number of freezing and thawing | compressive strength (kPa) |
|---|---|
| 0 | 2.77 |
| 1 | 2.89 |
| 3 | 3.54 |
| 5 | 3.75 |
| 6 | 3.82 |
| 8 | 3.81 |

Experimental Example 3: Measurement of Crosslinking Degree of Tissue Structure Mimetic by Ribose Crosslinking degrees of the tissue structure mimetic manufactured by changing concentration of ribose solution to 0, 1, 2.5, 5, 7.5, and 10% in Example 1 were measured. The crosslinking degrees were measured by quantifying hydroxylprolin. As the crosslinking degree was increased, an amount of hydroxyprolin to be measured was decreased. 5N HCl 1 ml was added to 5 mg of sample, and the obtained product was heated at 100 for 10 hours to be hydrolyzed. Calibration Curve was measured by using a hydroxyprolin standard material. One drop of 1% phenolphthalein was added to the standard material and the sample, and pH was controlled by 0.1 N KOH and 0.8 N KOH to obtain a pale pink product. 0.5 ml of 0.1M sodium borate buffer (pH 8.7) was added to each sample and mixed with each other. 2 ml of 0.2M chloramine T solution was added and reacted at room temperature for 25 minutes. 1.2 ml of 3.6M sodium thiosulfate was added, and 1.5 ml of KCl and 2.5 ml of toluene were added. An upper toluene layer was removed by centrifugation, and the obtained product was heated in boiling water for 30 minutes and cooled at room temperature. 2.5 ml of toluene was added, followed by centrifugation, and 1.5 ml of upper toluene layer was taken and moved into a new tube. 0.6 ml of Ehrlich's reagent was added and reacted for 30 minutes. The resultant solution was continuously mixed so as not to be separated into two layers, and absorbance was measured at 560 nm. Table 2 shows results values of crosslinking degrees depending on change in concentration of a ribose solution. According to Table 2, it could be appreciated that when the concentration of the ribose solution is 1%, crosslinking degree was 4%; however, when the concentration of the ribose solution is 2.5% to 7.5%, crosslinking degree was increased to be 11% to 32%. When the concentration of the ribose solution is more than 7.5%, crosslinking degree was not largely increased.

TABLE 2 crosslinking degrees depending on change in concentration of a ribose solution

| concentration of ribose (%, w/w) | crosslinking degrees (%) |
|---|---|
| 0 | 0 |
| 1 | 4 |
| 2.5 | 11 |
| 5 | 28 |
| 7.5 | 32 |
| 10 | 34 |

Experimental Example 4: Measurement of Compressive Strength of Each Tissue Structure Mimetic Compressive strengths of tissue structure mimetic manufactured by Examples 1 to 4 and the other company's product as a control group were measured. In the test method, span was controlled so as to meet a sample size according to ASTM D 638. Measurement device was UTM (WL2100), and measurement speed was 5 mm/min. 200N load cell was used, and the span (gauge length) was set to be 10 mm to measure each compressive strength.

Figure 4:
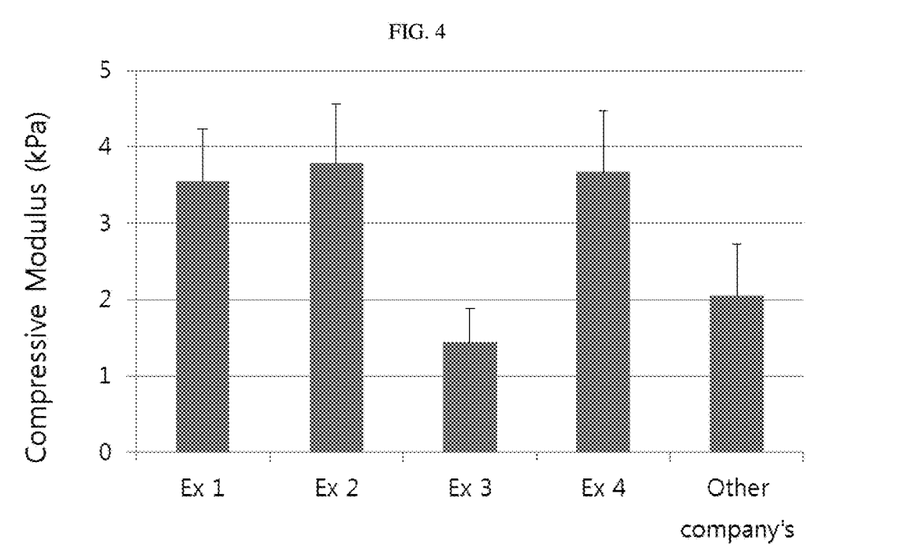
FIG. 4 is a graph showing comparison results between the tissue structure mimetic of the present invention and other company's product in view of compressive strength.

Table 3 shows values of compressive strength of each tissue structure mimetic, and FIG. 4 is a graph showing compressive strengths of each tissue structure mimetic. The tissue structure mimetic manufactured by Examples 1, 2, and 4 exhibited compressive strength of 3.55, 3.78 and 3.67 kPa, respectively, and the tissue structure mimetic having a low content of bone mineral component manufactured by Example 3 exhibited compressive strength of 1.44 kPa. The other company's product exhibited compressive strength of 2.05 kPa. It could be appreciated that the tissue structure mimetic manufactured by Examples 1, 2, and 4 had excellent mechanical strength, which are suitable for regenerating hard tissue, and the tissue structure mimetic manufactured by Example 3 was suitable for regenerating soft tissue.

TABLE 3 compressive strength of each tissue structure mimetic

|  | compressive strength (kPa) |
|---|---|
| Exampl 1 | 3.547 |
| Exampl 2 | 3.78 |
| Exampl 3 | 1.44 |
| Exampl 4 | 3.67 |
| commercial product | 2.05 |

Figure 5:
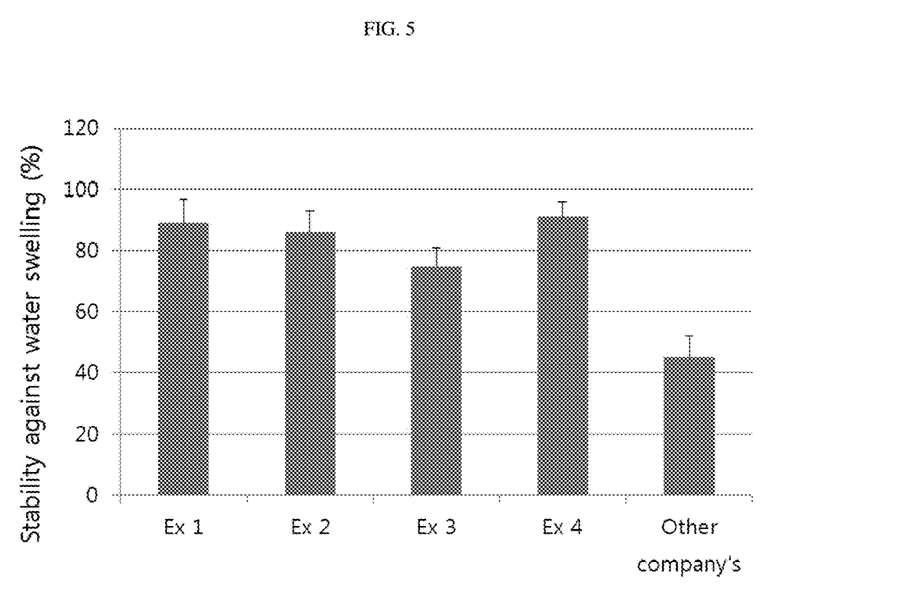
FIG. 5 shows results of stability against water-swelling of the tissue structure mimetic of the present invention.

Experimental Example 5: Stability Test of Tissue Structure Mimetic Against Water-Swelling The tissue structure mimetic manufactured by Examples 1 to 4 were evaluated in view of stability against water-swelling. Weights of the manufactured tissue structure mimetic and the other company's product were measured, respectively. Then, immediately after 1 mL of phosphate buffer was added thereto, excessive phosphate buffer was removed by filter paper, and weights were measured. When 1 hour passed after hydration, weights were measured to confirm structural stability. Table 4 shows results of stability against water-swelling, and FIG. 5 is a graph showing stability measurement results against water-swelling. In the other company's product that collagen was broken immediately during the hydration and spurt of bone mineral particles was confirmed, and weight thereof was largely decreased. However, the tissue structure mimetic manufactured by the present invention could be stably maintained in view of structure even though they were hydrated and swollen in a phosphate buffer, and weights thereof were not largely decreased. In addition, it was confirmed that spurt of the bone mineral particles contained in the tissue structure mimetic was inhibited.

TABLE 4 stability against water-swelling

|  | stability against water-swelling (%) |
|---|---|
| Exampl 1 | 89 |
| Exampl 2 | 86 |
| Exampl 3 | 75 |
| Exampl 4 | 91 |
| commercial product | 45 |

Experimental Example 6: Cell Differentiation Test

C2C12 (America Type Culture Collection, CRL-1772) in the tissue structure mimetic of Examples 1 to 3 were cultured in hard tissue-forming medium containing calcein (1 ug/mL, calcium fluorescent dye, green) for 14 days. The cultured cells were fixed by 2% glutaraldehyde solution. The fixed bone graft material was treated with 1% triton X-100, and DAPI solution (blue) was added thereto to stain nuclei. After the staining, the tissue structure mimetic samples were washed and fixed, then, as a last step of bone tissue differentiation, calcium deposited on the extracellular matrix was observed on the surface of the fixed bone graft material, by a confocal laser scanning microscope.

Figure 6:
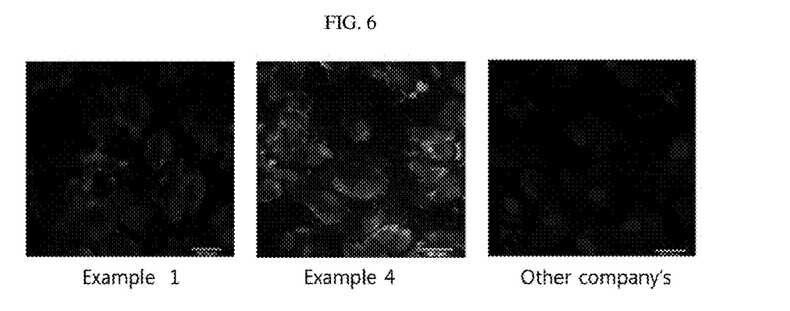
FIG. 6 is images of tissue structures mimic observed by confocal laser scanning microscope.

FIG. 6 is images of each tissue structure mimetic observed by the confocal laser scanning microscope. In the other company's product, deposited calcium was rarely observed; however, it was confirmed that calcium was deposited in the tissue structure mimetic manufactured by Example 1. In a case of the tissue structure mimetic containing peptide manufactured by Example 4, an amount of deposited calcium was increased. It could be appreciated that the tissue structure mimetic manufactured by the present invention were more effective for differentiation of bone cell, and in the tissue structure mimetic containing elastin-attached peptide, environment for tissue could be implemented to thereby provide a more excellent effect.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

INDUSTRIAL APPLICABILITY

In the tissue structure mimetic according to the present invention, bone mineral components are finely dispersed in the extracellular matrix protein to have excellent mechanical strength of the tissue structure mimetic and conductivity which provides a migration path of cells involved in tissue regeneration. In addition, environment of the tissue may be implemented by the peptide contained in the tissue structure mimetic to remarkably increase tissue regeneration capacity.

The invention claimed is:

1. A method for manufacturing a hard tissue structure mimetic which consists of a complex of extracellular matrix protein and bone mineral, and regeneration-functional peptide, the method comprising the steps of:
    (a) injecting a mixture of extracellular matrix protein and micro-sized bone mineral particles into a predetermined size of a forming mold;
    (b) repeating rapid-freezing and thawing thereby aligning a structure of protein;
    (c) crosslinking by adding a monosaccharide solution to form a complex of extracellular matrix protein and bone mineral;
    (d) binding a regeneration-functional peptide to said complex of extracellular matrix protein and bone mineral; and
    (e) performing lyophilization to yield said hard tissue structure mimetic,
    wherein the bone mineral is present, for regeneration of a hard tissue, at a content of 80 to 95% by weight, based on total weight of the complex of extracellular matrix protein and bone mineral.

2. The method of claim 1, wherein the extracellular matrix protein is at least one selected from the group consisting of collagen, hyaluronic acid, elastin, chondroitin sulfate, and fibroin.

3. The method of claim 1, wherein the bone mineral component is at least one selected from the group consisting of bio-derived bone mineral powders that are derived from aliograft, bovine hone, equine bone, swine bone, synthetic hydroxide apatite, and tricalcium phosphate micro powders.

4. The method of claim 1, wherein the regeneration-functional peptide is an elastin-attached peptide or a hyaluronic acid-attached peptide.

5. The method of claim 1, wherein the amount of the regeneration-functional peptide bound to said complex of extracellular matrix protein and bone mineral is in a range of from 1 to 1000 mg based on unit weight (g) of said complex in the tissue structure mimetic.

6. A method for manufacturing a soft tissue structure mimetic which consists of a complex of extracellular matrix protein and bone mineral, and regeneration-functional peptide, the method comprising the steps of:
    (a) injecting a mixture of extracellular matrix protein and micro-sized bone mineral particles into a predetermined size of a forming mold;
    (b) repeating rapid-freezing and thawing thereby aligning a structure of protein;
    (c) crosslinking by adding a monosaccharide solution to form a complex of extracellular matrix protein and bone mineral;
    (d) binding a regeneration-functional peptide to said complex of extracellular matrix protein and bone mineral; and
    (e) performing lyophilization to yield said hard tissue structure mimetic,
    wherein the bone mineral is present, for regeneration of a soft tissue, at a content of 5 to 35% by weight, based on total weight of the complex of extracellular matrix protein and bone material.

7. The method of claim 6, wherein the extracellular matrix protein is at least one selected from the group consisting of collagen, hyaluronic acid, elastin, chondroitin sulfate, and fibroin.

8. The method of claim 6, wherein the regeneration-functional peptide is an elastin-attached peptide or a hyaluronic acid-attached peptide.

9. The method of claim 6, wherein the amount of the regeneration-functional peptide bound to said complex of extracellular matrix protein and bone mineral is in a range of from 1 to 1000 mg based on unit weight (g) of said complex in the tissue structure mimetic.

10. The method of claim 9, wherein the regeneration-functional peptide consists of 5 to 30 amino acids, and the amount of the regeneration-functional peptide bound to said complex of extracellular matrix protein and bone mineral is in a range of from 100 to 500 mg based on unit weight (g) of said complex in the tissue structure mimetic.

* * * * *

UNITED STATES PATENT AND TRADEMARK OFFICE
CERTIFICATE OF CORRECTION

PATENT NO. : 10,232,083 B2  
APPLICATION NO. : 14/779339  
DATED : March 19, 2019  
INVENTOR(S) : Chong-Pyoung Chung et al.

Page 1 of 1

It is certified that error appears in the above-identified patent and that said Letters Patent is hereby corrected as shown below:

In the Specification

Column 4, Line 48: "e" should be -- in the --.

Column 6, Line 5: "inure" should be -- more --.

Column 6, Line 16: "n" should be -- invention --.

Column 6, Line 17 and 18: "glycerone" should be -- glycerose --.

In the Claims

Column 12, Line 8: "aliograft, bovine hone" should be -- allograft, bovine bone --.

Signed and Sealed this  
Twenty-third Day of July, 2019

Andrei Iancu  
*Director of the United States Patent and Trademark Office*